US005695975A

United States Patent [19]
Zimmerman et al.

[11] Patent Number: 5,695,975
[45] Date of Patent: Dec. 9, 1997

[54] **MATING PROCESS FOR PREPARING *OPHIOSTOMA PILIFERUM* FUNGI FOR PITCH REDUCTION**

[75] Inventors: Wendy C. Zimmerman, Watertown; Roberta Lee Farrell, Groton, both of Mass.

[73] Assignee: Clariant Finance (BVI) Limited, Tortola, Virgin Islands (Br.)

[21] Appl. No.: 471,552

[22] Filed: Jun. 6, 1995

Related U.S. Application Data

[62] Division of Ser. No. 267,684, Jun. 28, 1994, Pat. No. 5,607,855, which is a continuation of Ser. No. 138,174, Oct. 15, 1993, abandoned, which is a continuation of Ser. No. 899,796, Jun. 17, 1992, abandoned.

[51] Int. Cl.$^6$ .............................. C12N 15/00; C12N 1/14
[52] U.S. Cl. .................................. 435/172.2; 435/254.1
[58] Field of Search .............................. 435/172.2, 254.1, 435/172.1, 267, 277, 278, 911; 8/401; 162/9, DIG. 4, DIG. 12, 12

[56] References Cited

U.S. PATENT DOCUMENTS 3,486,969 12/1969 Nilsson et al. .

FOREIGN PATENT DOCUMENTS

| 0387187A2 | 9/1990 | European Pat. Off. . |
| 0470929A2 | 2/1992 | European Pat. Off. . |

OTHER PUBLICATIONS

Abstract CA118(4):23944e.
Abstract CA117(6):51099f.
Abstract 92:320935 CA previews.

*Primary Examiner*—Irene Marx
*Attorney, Agent, or Firm*—Hesna J. Pfeiffer; Michael P. Morris

[57] ABSTRACT

This invention relates to a method of obtaining a fungus of the species *Ophiostoma piliferum* by selective mating of strains of the fungus and selecting for an ascospore offspring which grows white or colorless, and has the ability to reduce pitch in Southern Yellow Pine wood chips.

6 Claims, No Drawings

MATING PROCESS FOR PREPARING *OPHIOSTOMA PILIFERUM* FUNGI FOR PITCH REDUCTION

This is a division of application Ser. No. 08/267,684, now U.S. Pat. No. 5,607,855, filed Jun. 28, 1994, which in turn is a continuation of application Ser. No. 08/138,174, filed Oct. 15, 1993, which in turn is a continuation of application Ser. No. 07/899,796, filed Jun. 17, 1992, the latter two of which are now abandoned.

This invention relates to fungi having particularly desirable overall properties for reducing the pitch content of pulpwoods and pulps, and to the preparation and use of such fungi.

In published European Patent Application 0387187A2 (based on U.S. application Ser. No. 310,814, filed Feb. 13, 1989), now abandoned there is described the application of certain wood-penetrating fungi to pulpwoods and pulps to reduce the pitch content thereof. Similarly useful fungi which have growth virulence similar to those of natural isolates but which are lighter in color and preferred for use in such process are described in published European Patent Application 0470929A2 (based on U.S. applications Ser. Nos. 560,521 and 657,581, filed Jul. 31, 1990 and Feb. 19, 1991, respectively) both abandoned. The disclosures of both said published European Patent Applications (and their U.S. counterpart applications) are hereby incorporated herein by reference.

Such fungi, which are of the classes Ascomycetes and Deuteromycetes, are applied or distributed upon pulpwood forms such as wood chips, sawdust or logs, or first stage mechanical pulp, and the resulting treated substrate maintained under conditions under which the fungus grows, for a time sufficient to reduce the pitch content of the pulpwood. Such process is judged of considerable importance in reducing the substantial amount of downtime caused by pitch deposits and accumulations in the pulp and paper and other industries which convert pulpwoods, and has already been proved commercially successful. Improved physical or strength properties of ultimate products such as paper are also indicated, translating to greater production rates, and the process provides other practical advantages.

A preferred fungal species for such process is *Ophiostoma piliferum* and the isolates C-1 Det 84 and WZ58 which are identified in European Application 0470929A2 are natural mutant (Ascospore) strains which grow light in color but virulently on non-sterile pulpwood substrates. Such fungi grow effectively on a wide variety of woods and are particularly useful on pine, e.g. Southern Yellow Pine, and on certain hardwoods. An isolate such as C-1 Det 84 and WZ58, can be used to improve brightness on non-sterile substrates which in the absence of any treatment would suffer brightness loss during storage as a result of natural fungal infestation.

In our prior efforts we emphasized growth virulence and light color as a challenge to be overcome in providing desired improved fungi for the process, while maintaining good pitch degradation properties in selected candidates. While pitch degradation ability and growth virulence were indicated not to reflect the same properties, and in this respect pitch degradation level was unpredictable, it was satisfying to find that the white growing WZ58 was at least as good as the best of its darker parents in pitch degradation and even rivaled our dark TAB 28 standard on sterile Southern Yellow Pine wood chips.

Our continuing efforts have sought to find out whether it might be possible to significantly exceed the pitch degradation ability on pine of WZ58 and more particularly to exceed our dark TAB 28 standard in an essentially white or colorless growing fungus which would also have at least the desirable growth virulence of WZ58. We were also interested to see if it was possible to improve the pitch degradation ability of WZ58 against important hardwoods such as aspen.

DESCRIPTION OF INVENTION

In accord with the invention, it has been found that the mating of two non-white *Ophiostoma piliferum* strains herein identified as TAB 28 and TAB 51 can produce virulently growing non-white, intermediate strains, herein represented by the strain identified as D3, having significant improvement in pitch degrading ability relative to both said parents and levels previously obtained by us, and that such intermediate can then be further mated with our white growing WZ58 to obtain virulent, white growing fungi having at least the pitch degrading ability of the non-white intermediate D3. It has been also found that the mating of such intermediate strain can produce virulent, white growing fungi having pitch degrading ability which even exceeds that of the already significantly improved intermediate fungus.

Accordingly, the present invention provides new strains of *Ophiostoma piliferum* which are characterized by not only growing white or colorless and by having good growth virulence, but which also exhibit exceptional pitch degradation properties.

In a particular aspect, the *Ophiostoma piliferum* fungi provided by the invention grow white or colorless with at least the same growth virulence as WZ58 on sterilized Southern Yellow Pine pulpwood while reducing the pitch content thereof considerably better than WZ58, the degree of improvement being at least 10%.

Such fungi also are similarly improved in pitch reduction compared to our dark standard TAB 28 and may perform better on certain hardwoods such as Aspen than other white isolates such as WZ58, the improvement on Aspen being of the order of at least 5%, usually about 10%, over said WZ58.

As a result of producing our new white growing fungi, new non-white intermediate fungi, typically of a gray color, e.g. medium to dark gray, herein exemplified by the strain D3, with good growth virulence and pitch reduction capability superior to both TAB 28 and WZ58 on Southern Yellow Pine, may also be obtained.

The potent pitch degrading fungi of the species *Ophiostoma piliferum* that have good growth virulence and ability to grow white and/or virtually colorless on a wood substrate are obtained in accord with the invention by: a) mating two dark growing fungal parents herein identified as TAB 28 and TAB 51, b) selecting a non-white ascospore offspring which is matable with the fungus herein identified as WZ58 and which has improved ability to reduced pitch content of the sterilized wood relative to both parents in no more than 21 days growth, preferably in no more than 14 days growth, while growing at least as virulently as both parents on the sterilized substrate when evaluated in the period of 10 to 11 days growth, c) mating such offspring with the white growing fungus herein identified as WZ58; and d) selecting at least one ascospore offspring from the mating in c), above, which is characterized by i) growing white on the sterilized substrate, ii) growing at least as virulently as said non-white offspring on the sterilized substrate when evaluated in the growth period of 10 to 11 days; and iii) having ability to reduce pitch in the sterilized substrate at least as effectively as said selected non-white offspring after no more than 21 days growth, preferably no more than 14 days growth. The primary sterilized substrate for use in the evaluations required in the above method is Southern Yellow Pine in the form of wood chips.

As used herein with reference to the color produced on wood chips, the term "white" is meant to include both essentially white and essentially colorless, and mixed effects of white and colorless. The term "non-white" indicates a color distinctly darker than white ranging from shades of gray through blues, brown, blue-black and black, the latter two being typical of native blue stain fungi.

In Step b), above, the non-white offspring desirably exhibits at least a 5% improvement in pitch reduction over the best of its parents, preferably at least 10%. Such offspring are preferably of a shade ranging from medium gray to the darker color of the typical native blue strains, e.g. dark gray, blue-black or black, or may be a mutant color such as medium to dark brown, when grown on the sterilized substrate for 10 to 11 days.

In Step d), it will be apparent that white fungi are obtainable which degrade pitch at least 5% better than the best of the parents mated in step a), preferably 10% better. More preferably, an ascospore with further improvement of at least 5% over the pitch degrading ability of the offspring selected in Step b) is selected or the final ascospore is at least 15% improved in such ability over the best of the parents mated in Step a). While virulence is measured above on sterile wood, it is desirable that final ascospores selected in Step d) demonstrate a growth virulence at least about equal to that of the original parents in Step a) and the offspring selected in Step b) on fresh, non-sterile wood as hereinafter described.

The invention includes not only individual ascospore isolates and their resulting fungi but also all of the additional derivatives obtainable therefrom, particularly those embodying at least the level of desired properties of the parent ascospore. A finally selected ascospore fungus may be mated to provide a heterokaryotic fungus for use in pitch degradation, but this is not preferred as the heterokaryons have been found to tend to be unstable in one or more desired properties during repeated growth or large scale growth. The ascospore may also be mutated to provide other desirable derivatives, including man-made mutations, and those which at least substantially embody the desired improved properties of the ascospore selected in step d) are also included in the invention.

Procedures for the generation, general separation, dispersal and individual isolation of ascospores and the growth and isolation of fungi they generate are well known. A representative literature reference is, for example, Upadhyay, H. P. (1981), A Monograph Ceratocystis and Ceratocystiopsis; University of Georgia Press, Athens, pages 28–29. A publication with specific to ascospores of Ophiostoma is Brasier, C. M. and J. N. Gibbs (1976), Inheritance of Pathogenicity and Cultural Characters in *Ceratocystis ulmi:* Hybridization of Aggressive and Non-Aggressive Strains; Ann. Appl. Biol. 83, 31–37. In general, the parent fungus (or fungi) is cultured to the stage where ascospore generation is sufficiently complete and the ascospores sufficiently liberated from the fungal mass or secreted that the ascospores as a mass or collection can be generally separated or recovered, for example, by picking all or one or more portions of the viscous, hydrophobic ascospore-containing material at the top of the perithecium with a sterile dissection needle and transferring to a specialized spore suspension medium such as pinene which will dissolve the hydrophobic material and free the spores into the suspension medium. The medium (or portions thereof) containing the ascospores is then diluted and the dilution spread on plates containing a suitable growth medium for development of a solid phase fungal growth in a manner which allows the ascospores to develop or grow into discrete or individual fungus colonies which can be picked or isolated for further growth in individual cultures, e.g. liquid culture, to provide inoculum for evaluation of the fungus produced or generated from the individual ascospores.

It has been found that very high and suitable counts of viable ascospores of the subject pitch-degrading fungi may be obtained by taking up or dispersing the ascospores in their hydrophobic carrier as recovered from the fungal culture in a non-toxic oil which effectively dissolves the hydrophobic material to free the spores into the oil and which is consumable (as a food or carbon source) by the fungus, preferably a vegetable oil such as corn oil, and then treating the ascospore-containing oil with a non-toxic (to the fungus or its spores) oil dispersing agent which may be of any of the many known types for dispersing such oils, such as the well known Triton X-100. The spreading or plating out of the dispersing agent-treated oil results in large number of discrete, viable ascospore-containing droplets of said oil and, additionally, the oil is consumed and removed from plates as the fungus grows, leaving discrete fungal colonies which can be readily recovered and further cultured for evaluation. The large number of viable ascospore fungi obtained for screening by the indicated isolation method is important in achieving objectives, since only a very low percentage or number of a very large number of ascospore fungi are indicated to provide the sought-for improved properties.

Inoculum for use in the invention may be any cellular form of the white growing fungi provided by the invention that results in growth of the fungus which is placed on a substrate such as wood. Such forms include mycelia, spores and whole or part of cultures of the fungus, and dry forms such as freeze dried powders and the like. Inoculums may include various additives such as preservatives and carriers which may be solid or lilquid carriers. Dry forms such as freeze dried powders may be applied as such, but are preferably diluted with water.

Other Preferred Embodiments and General Evaluation Standards

A determination of whether or not the criteria of this invention are satisfied will be conducted on a laboratory scale. While reference may be made to the Experimental Section herein for guidance in certain cases, the determination will be made in accord with the description and discussion under this paragraph heading and the next two paragraph headings (Other Laboratory Evaluation Standards and Evaluation Procedures), and it is not represented that the experiments in the Experimental section conform exactly in every aspect to such determination description.

With regard to pitch reduction, such evaluations are carried out on sterile substrates to eliminate the influence of other organisms which naturally infect non-sterile substrates. The evaluations are made in 14 days after inoculation.

With regard to any evaluation concerning brightness, these evaluations are desirably conducted for screening purposes on sterile substrates to again eliminate the influence of organisms which naturally infect non-sterile substrates and obtain a more absolute assessment of the color influence of the candidate. These evaluations will be conducted after growth for 21 days.

Growth virulence determinations may be conducted on both a sterile and non-sterile substrate and made 10–11 days after inoculation to reflect the desired fungi provided by the invention. Such determinations are made as herein further described, on the basis of percentage of substrates or wood chips showing growth of the candidate compared to growth of a referenced parent or fungus. Such determinations may be made on a percentage basis and, when an improvement in virulence is a criteria to be satisfied, an improvement of at least about ten percentage points.(i.e. 80% to 90%) is usually sought to reduce error and provide statistical confidence. When the determination is made for virulence and both the referenced parent and offspring fungus show 80% or better growth, the evaluation/criteria dosage of $10^{10}$ CFU is reduced until the referenced parent growth is less than 70%, e.g. 35–65%. For screening purposes herein, the determination is made on a sterilized substrate.

Preferred fungi of the invention are those which effect desired results on at least Southern Yellow Pine at dosages not exceeding $10^{10}$ CFU/Kg., particularly at dosages not exceeding $10^9$, and especially dosages not exceeding $10^8$.

Especially preferred ascospore fungi provided by the invention are those showing at least about the same growth virulence as TAB 28 on a non-sterile substrate but which grow essentially white on the sterilized substrate, e.g. a Southern Yellow Pine substrate, and which reduce pitch on the sterilized substrate at least 10% better than TAB 28.

A suitable product form of the fungi of the invention is obtained by fluid bed drying of a mixture of a spore-containing fermentation concentrate, resuspended in water, and inert solid which does adversely affect the stability of the spores, e.g. a clay such as Kaolin clay. Another suitable product form, preferably without added carriers, is produced by freeze dry techniques, and such products may for acceptable periods be stable at room temperature when maintained under vacuum.

Other Laboratory Evaluation Standards

In carrying out the invention to isolate desired ascospore fungi meeting criteria in accord with the invention, various comparative evaluations will be made on pulpwood substrates to determine pitch reduction, brightness and virulence. These will be conducted on a laboratory scale. While the substrate may be of different pulpwood forms, we judge the criteria standard and more suitable form to be wood chips. The substrates will be obtained from fresh cut timber or logs stored at room temperature for seven (7) days immediately after cutting, and then made into wood chips which are promptly subjected to evaluation (or stored for a brief period at 50° C.). Wood chips showing after such seven days anything other than isolated or very minor visible growth of native fungi such as blue stains, papulaspora and trichoderma are rejected. Such substrates are selected to be free of knots. Each evaluation will be done on substrates of the same wood species and on substrate samples obtained from the same timber or log, and at the same time after cutting of the tree. A collection of such substrates will be thoroughly mixed to disperse isolated pieces which may be naturally infected or more heavily infected with microorganisms. Individual sample lots of equal size (weight) and amounting to 200–400 grams each will be taken from the collection. Samples to be sterilized are heated in an autoclave at 120° C. for 45 minutes. Evaluations on non-sterile substrates may be started 7 days after cutting of the tree. Evaluations for comparison on sterile substrates are commenced at roughly the same time or slightly later, preferably after wood chips from the cuttings have been sterilized and allowed to completely cool to room temperature (ca 20° C.). The inoculum will be applied as a concentrate or deionized water dilution from a culture at an inoculum concentration which together with the manner of using it to inoculate will not introduce more than about 1 ml. of water for each 100 g. of substrate. The dosage itself will be expressed in colony forming units representing the count by standard procedures of the total of viable mycelia and/or viable spores in the inoculum. The dosage applied will be same and not exceed the criteria maximum of $10^{10}$ CFU/kg. of substrate (prior to sterilization in the case of the sterilized sample). The inoculum will be in a form as similar as possible for the referenced parent fungus and ascospore fungus being evaluated. Hence, if the inoculum for one is essentially only mycelia, the inoculum for the other will be essentially only mycelia and harvested at an equivalent growth stage. In a like manner, mixtures of spores and mycelia will be in the same proportions. If the fungus can provide a high proportion of spores (75% or more of CFU) in culture, as is usually the case, an inoculum which is 75% or more spores of similar characterization will be used. Hence, if the fungus forms a high proportion of blastospores, such an inoculum will be used. The inoculation of the substrate will be done in a manner suited to contacting as many individual wood pieces as reasonably possible, even though initially only 10–30% of the chips may be actually contacted. The wood chip substrates will be placed in clear plastic bags of good size and the chips in the bag rested and spread out on a flat surface. The inoculum will be applied with an eyedropper by placing no more than one drop on individual chips. The bag is then sealed and the chips mixed/shaken thoroughly for 10 seconds to distribute the inoculum to other chips. The bag is then tightened or further closed around the chips if necessary to have good contact among chips in a pile-like accumulation. All inoculated substrates will be stored in the dark and then evaluated, the storage being done at room temperature except in the cases as indicated above. Each evaluation as above described will be run in triplicate and the results averaged, and each triplicate series will again be repeated three more times (total of four triplicate series) but using in each series samples from a different tree of the same species and variety within the same forest location.

Evaluation Procedures

A) The pitch content of substrates is determined in accord with the standard TAPPI Procedure T204 OS-76 and may be expressed as mg. of pitch content per gram of substrates which had been extracted with DCM (a.k.a. methylene chloride). As used on a substrate such as wood chips, the treated chips are splintered with pruning shears to a width of about 1 cm, then dried overnight at 60° C. and then ground into sawdust using a Thomas-Wiley Intermediate Mill with a 10-mesh screen (10 gauge wire screen), and dried again overnight at 60° C. Three (3) grams of dried sawdust are combined with about 30 ml. of DCM and the resulting mixture agitated overnight (about 15 hours) at room temperature. The liquid medium is pipetted from the mixture, filtered through a 0.45 micron organic filter, the liquid allowed to evaporate at room temperature overnight (for about 15 hours) in a preweighed dish and the residue oven-heated at 60° C. for 30 minutes to further remove DCM. The weight of the residue is determined in mg. as the pitch content and expressed either as mg. of pitch content per gram of substrate or as a percentage of pitch in original the substrate (% extractives).

B) Substrate brightness is determined on 10 gauge sawdust and substrates such as wood chip will be first splintered using pruning shears to about 1 cm. and then ground using a Thomas-Wiley Intermediate Mill with a 10 gauge wire mesh screen, with intermediate dryings at 60° C. as indicated in A), above.

Brightness is measured on a Photovolt Reflection meter model 670. The meter is a separate unit from the photocell and the photocell can be turned upside down if desired. Using the above instrument, our procedure is as follows:

1. Calibrate the reflection meter with an enamel plaque calibrated in terms of paper brightness (75.0). Place the plaque on a petri dish and present it to the search unit (photocell). Adjust the meter reading to the value on the enamel plaque. The standard reading may be set this way or by placing the standard inside the petri dish so it is flush with the plastic. It is separated from the dish by any distance.

2. Fill the petri dish with an even layer of sawdust, about 10 g or less, and present the dish to the search unit and take five readings from various regions on the dish. The average of the five readings is the brightness of the sawdust. A new petri dish is used for each sample and each replication.

C) Growth or virulence of a fungus will be measured for comparison among fungi and all possible conditions, unless otherwise specified, will again be made as identical as possible for the comparison. Growth or virulence is determined by a relatively simple visual observation protocol applied on a consistent basis, and carried out immediately at the end of the 10 day test period. The protocol is based on color categories of growth which can be observed or ascertained on each individual wood chip or substrate with the unaided eye at normal reading distance. One color category, typically the lightest, will represent the growth color of the ascospore candidate or lightest growing candidate if several are to be compared with each other. Categories of white (w.), gray (g.) and black (b.) may be used as well as the five categories of white (w.), light gray (l.g.), medium gray (g.), dark gray (d.g.) and black (b.) depending largely on the color of ascospore candidate to be compared with its referenced parent fungus or the number of such candidates. The five color rating category is preferred as all candidates can be usually assigned into one of the five. The number of chips observed to have the .color growth of the ascospore candidate is totalled in essentially four categories as used in the evaluations reported hereinbelow, viz. a single plus (+) is assigned when about 25% of the chips show growth of the particular ascospore candidate, two pluses (++) when about 50% show growth, three pluses (+++) when about 75% show growth and four pluses (++++) when about 100% show growth. If a percentage within about 5% points of an intermediate percentage, e.g. 58% is within 5% points of 62.5%, a plus is added after a slash mark and the lower rating, e.g. (++/+) or by (++/+++). In an analogous manner an intermediate rating below the first level rating is indicated by (+/−). A similar totalling will be made for the parent(s) to be referenced. For purposes of making more precise evaluations relative to the criteria described herein, when needed, an actual percentage will be determined and the percentages compared. However, a margin of error will be allowed for human error, the greater difficulty of ascertaining lighter growths and the substantial achievement of the objectives of the invention. Such margin is 10 percentage points, such that an ascospore candidate found growing on say 78% of wood chips will be considered of equal growth ability or virulence as a parent fungus which gives a percentage of 88%. Non-sterile, treated chips will usually show growth in other areas of the chip of other organisms, commonly black coloring fungi, and such background growth coloring may be separately recorded. Such background growth does not change the evaluation being made but does indicate the presence of fungi which have naturally infested the pulpwood.

Deposits

We have deposited with the Northern Regional Research Center (NRRL) at Peoria, Ill., U.S.A. the following fungi referred to herein, which were assigned the Accession Numbers given below along with their date of deposit.

| Fungi | Accession No. | Deposit Date |
| --- | --- | --- |
| TAB 28 (*O. piliferum*) | NRRL 18690 | July 23, 1990 |
| TAB 51 (*O. piliferum*) | NRRL 18754 | Jan. 24, 1991 |
| WZ58 (*O. piliferum*) | NRRL 18755 | Jan. 24, 1991 |
| D97 (*O. piliferum*) | NRRL 18917 | Nov. 12, 1991 |
| D3 (*O. piliferum*) | NRRL 18918 | Nov. 12, 1991 |

The deposits were made under the Budapest Treaty for this application. However, the NRRL were instructed to make generally available to the public, upon deposit, the fungi C-1 and TAB 28. In connection with the above deposits, D3 is also identified as T28T5103 and D97 is also identified as WZ5803D97.

Experimental

Ascospores of *O. piliferum* are produced in specialized reproductive structures called perithecia. The ascospores are produced in asci within the base of perithecium. As the ascospores mature, the asci autodeliquess and the ascospores are secreted in a droplet of viscous hydrophobic material at the top of the perithecium. Isolation of the ascospores may be effected with pinene as recommended in the literature. However, ascospore isolation was considerably less than desired with pinene and, as an alternative, we found that a sterile vegetable oil/detergent treatment produced a very high degree of the desired dispersal of the ascospores and was non-toxic. In fact, the vegetable oil is consumed by the fungus as an apparent food (carbon source) in a manner judged analogous to the consumption of pitch, and hence the method may be applied to any fungus which consumes pitch. The consumption of the oil was also a very fortuitous manner of eliminating the solvent (oil) for the hydrophobic material.

The ascospores were diluted 100 fold in sterile corn oil, then two separate additional dilutions, 10 and 100 fold in sterile 10% Triton X100 were made for comparison to each other. 100 ul aliquots of the two dilutions were plated on YMA to achieve plating densities of 100 and 10 spores per plate. Triton X100 was used to disperse the corn oil and prevent reaggregation of the oil droplets on the surface of the agar.

The fungi removed the oil from the plates as they grew. In the presence of oil/detergent, colonies remained discrete and quite compact, and slowly achieved pickable size, and were ready in 7 days. When the individual colonies were large enough to restreak, all of the colonies from the lower dilution plates, regardless of size or coloration, were transferred to fresh YMA and grown for one week prior to testing for perithecia production (homokaryon status).

The isolates were screened in order to eliminate as many heterokaryons as possible.

Screening was carried out by streaking each isolate on wood chip agar and monitoring for perithecium production over a 2 month period.

Isolated which did not produce perithecia were discarded.

Among the dark isolates (dark gray to black), 20 of the more apparent virulent isolates were screened for growth virulence and pitch reduction on sterilized Southern Yellow Pine wood chips by the test procedures herein described. As a result of this screening the isolate designation D3 was selected as an isolate which grew as virulently as TAB 28, the more virulent of the parents, and which demonstrated a significantly increased ability to degrade pitch compared to both parents.

The ascospore D3 was then mated with WZ58 by the same procedure employed to mate TAB 51 and TAB 28, except that the suspension examined in the hemocytometer counting chamber showed $1\times10^6$ cells/ml. of which 97% were single ascospores.

No isolates were discarded as heterokaryons by the perithecia evaluation but several grew patchy with both black and white hyphae, and were discarded (as unacceptable and possible heterokaryons, although they were not self-fertile). Among the remaining healthy ascospore isolates, 53 were black, 3 were gray and 43 grew white and/or essentially colorless. The white isolates were then screened for pitch degradation ability and growth virulence and several candidates selected for rescreening.

For rescreening, each isolate was cultured in YM at room temperature, 200 rpm for 62 hours. Blastospores (with about 5% mycelia) were harvested by centrifugation and resuspended in sterile water to a viable CFU of approximately $10^8$/ml. The viability of each inoculum was tested and found to be 50% or better.

It was noted that the ascospore fungus D3 was of the same mating type as its offspring herein identified as D97 (our mating type A) whereas WZ58 was of the opposite mating type (type B). The fungus D3 can therefore be further mated with D97 if desired.

All chips employed were southern yellow pine and 100 g aliquots of sterile (autoclaved chips) wood chips were inoculated in duplicate with 1.0 ml of fungal suspension. The inoculated chips were stored at room temperature in the dark. Growth was monitored with time over a period of eleven days. Results are reported below in Table A (wherein isolates numbered D37 or higher are selected from the mating of WZ58 and D3).

TABLE A

Growth on Sterile Chips

| Fungus | 3 days | 5 days | 7 days | 11 days |
|---|---|---|---|---|
| control | − | − | − | − |
| WZ58 | +++/++++w | ++++w | ++++w | ++++w |
| D3 | +++g | +++/++++lg | +++g | +++dg |
| C-1D5 | ++++w | ++++w | ++++w | ++++w/lg |
| TAB28 | +++/++++lg | +++g | ++++b | ++++b |
| D37 | +++/++++w | ++++w | ++++w | ++++w |
| D47 | +++w | ++++w | ++++w | ++++w |
| D49 | ++++w | ++++w | ++++w | ++++w |
| D53 | +++/++++w | ++++w | ++++w | ++++w |
| D59 | ++++w | ++++w | ++++w | ++++w |
| D62 | +++w | ++++w | ++++w | ++++w |
| D85 | +++/++++lg | +++g | ++++b | ++++b |
| D86 | +++w | +++/++++lg | ++++b | ++++b |
| D87 | +++/++++w | +++/++++w | ++++w | ++++w |
| D89 | +++/++++w | ++++w | ++++w | ++++w |
| D91 | +++/++++g | +++g | ++++b | ++++b |

TABLE A-continued

| D95 | +++/++++lg | ++++g | ++++b | ++++b |
|---|---|---|---|---|
| D97 | ++++w | ++++w | ++++w | ++++w |
| D99 | +++/++++w | ++++g | ++++b | ++++b |

Legend:

| Coverage of chips: | | Color of Fungal Growth | |
|---|---|---|---|
| − | no visible growth | w | white |
| + | 25% of the chips covered | lg | light gray |
| ++ | 50% of the chips covered | g | gray |
| +++ | 75% of the chips covered | dg | dark gray |
| ++++ | 100% of the chips covered | b | black |

Fungi for pitch degradation experiments were cultured in YM at room temperature, 200 rpm for 3 days. Cells (about 95% blastospores) are harvested by centrifugation and resuspended in sterile water to approximately a viable CFU of $1\times10^8$/ml. Four replicate 400 g bags of sterilized Southern yellow pine wood chips were inoculated with 4.0 ml of fungal suspension. The inoculated and control bags are incubated at room temperature in the dark for two weeks. Results are reported below in TABLE B along with measurement of brightness of the isolates.

TABLE B

PITCH DEGRADATION

| Strain | % Extractives - 4 Replicates - mean | Brightness mean |
|---|---|---|
| Control | 4.53 | N.A. |
| TAB28 | 2.95 | 35.4 |
| WZ58 | 2.82 | 75.5 |
| D3 | 2.51 | N.A. |
| D59 | 2.59 | N.A. |
| D62 | 2.86 | 74.5 |
| D97 | 2.24 | 72.9 |

White isolates showing improved reduction of pitch on Southern Yellow Pine were also screened for pitch reduction on Aspen. Results are reported below in Table C.

TABLE C

| Strain | % Extractives mean | Brightness |
|---|---|---|
| Control | 2.86 | 67.7 |
| TAB 28 | 2.12 | 43.3 |
| WZ58 | 2.42 | 67.2 |
| D59 | 2.46 | 65.4 |
| D97 | 2.22 | 69.2 |

Strains D59 and D97 are the first white strains to show significantly greater pitch reduction than WZ58 on Southern Yellow Pine (TABLE B). Strain D97 is the only strain further improved in pitch reduction over the D3 intermediate (TABLE B). Strain D97 is also the only white strain to show significantly greater pitch reduction than WZ58 on aspen (TABLE C).

Growth Virulence on Non-Sterile Substrates

Non-sterile Southern Yellow Pine woods prepared as indicated above were inoculated with D97 which was harvested after 62 hours ($10^8$ CFU/ml.) at a rate of $10^8$ CFW per kilogram of wood chips. Evaluation of growth is reported below in Table D, with other fungi for comparison.

TABLE D

| Fungus | 7 days | 10 days |
|---|---|---|
| TAB28 | ++/+++w/g | +++/++++b |
| D3 | ++g | +++/++++b |
| WZ58 | ++/+++w | +++/++++w |
| D97 | +++/++++w | +++/++++w |

In Table E about 25% of the wood chips treated with WZ58 and D97 showed some gray to black growth.

Fermentation and Formulation

Cells (blastospores) of D97 are fermented at 25° C. (50 liter fermentor) in media containing 200 g. per liter malt extract and 20 g per liter yeast extract until cell density is $3 \times 10^9$ cells/ml. The fermentation media (CA.36–48 hours) aerated (oxygen levels near saturation, i.e. not limiting at any point during fermentation). The fermentation media is allowed to rise to pH 6.0–6.5 or is adjusted to such level with sodium hydroxide.

Fluid Bed Method and Product

The biomass grown in the fermentor is harvested by centrifugation; pH is measured and adjusted to 6.0–6.5 if necessary, and the cells (15–20% solids) mixed with clay at a ratio of 1 part wet biomass (approximately 20% solids) to 2 parts dry Kaolin clay. The moisture content of the biomass clay mixture ranges from 25–30%. The flowable mixture is loaded onto an Aeromatics fluid bed dryer and subjected to drying under ambient temperature conditions to a final moisture content of 5–10%. Outlet air temperature is maintained below 35° C. Drying time is from 20 to 40 minutes. Fluid bed dried material retains viability and the ability to grow on non-sterile wood chips and reduce pitch levels after prolonged storage of the dried material at –15° C. Stability data is given below in Table E.

TABLE E

| storage time (Days) | Colony forming units/gram |
|---|---|
| 0 | $5 \times 10^9$ to $7 \times 10^9$ |
| 166 | $2 \times 10^9$ to $3 \times 10^9$ |

The number of cells is determined employing standard assay techniques with a Hemocytometer with V-load system, Neubauer rulings 0.1 mm below 0.4 mm cover glass and using the Olympus Model BHS Phase/Fluorescent Research Microscope with Ultra-violet excitation cube with bright lines at 334 and 365 mm for Leucophor® B150 staining and a Blue excitation cube with bright lines at 435 mm and spectrum regions near 490 mm, together with an exciter yellow filter at wavelength 455 mm for fluorescein acetate staining.

Freeze Method and Product

Blastospores of D97 are fermented at 25° C in a 250 liter fermentor. The media contains 200 g/L malt extract and 20 g/L yeast extract. The cells are fermented for 64 hours and the oxygen level is kept at saturation. The fermentation media is allowed to rise to pH 6.0–6.5 or is adjusted to such level with sodium hydroxide.

Cells are harvested with the Westphalia SB7 centrifuge. Cell paste, after pH checking and adjusting to 6–6.5 if necessary, is frozen in 1 g aliquots by placing in a freezer set at –70° C. Samples are then dried for 8 hours on the Labconco lyophilizer at an internal temperature in the dial range of –50° C to –150° C. (final moisture is 10%). Samples are then stored at –15° C and are found to remain essentially stable over a period of at least 60 days.

Limitations on equipment available to us are believed to restrict lyophilization temperatures to about –50° C. to –70° C. It is indicated that lyophilization temperatures may be considerably lower, e.g. from –90° C. to –300° C. and that lower temperatures may be preferred in large scale operation with equipment capable of such operation. In such large scale operations, cell slurries or pastes, e.g. a slurry of 15% solids, may be frozen as thin sheets in pans over a period of at least 4 hours, preferably at least 8 hours, at –50° C. The frozen material, as such or broken up, is then lyophilized in an internally cooled vacuum freeze drier for 24–36 hours. Final moisture contents may be reduced to as low as 3%, or even lower. Products produced by lyophilization in product forms such as freeze dried powders may exhibit room temperature stability when maintained under vacuum (vacuum packaged) for reasonable periods, e.g. at least 30 days.

The term "pulpwood" as used herein means any harvested (cut down) form of a tree material used in making paper, cardboard or other cellulosic product such as viscose, but prior to pulping, and includes such forms as timber, logs, wood chips, sawdust and the like. The term "refined pulpwood" means a pulpwood resulting from the application of mechanical and/or shearing forces to whole pulpwood forms such as logs to obtain a multiplicity of high surface area, small pieces, such as wood chips and sawdust, which are introducible into a pulping process. The term first stage mechanical pulp means a pulp, isolated from a mechanical pulping process, which contains 60% or more of the lignin content of the substrate prior to pulping.

The fungi provided by the invention may be used to reduce the pitch content of pulpwoods and first stage mechanical pulps as described in patents and applications incorporated by reference. Basically, an inoculum of at least one of the fungus is applied to the substrate(s) and the inoculated substrate(s) maintained at a growth temperature of the fungus, e.g. 35°–90° F., for a time sufficient to degrade the pitch content of the substrate, e.g. 5–14 days. Refined pulpwoods are generally accumulated, e.g. in a pile, after inoculation which will be desirably representatively distributed throughout the accumulation. Such accumulation may be in the form of a typical wood chip pile or in a container or enclosed space such as a rail car, ship or the like to allow pitch reduction to the effected during transport. Timber, logs and the like may be treated in many fashions to induce growth in a major portion or more of such substrate, e.g. timber or logs may be scored lengthwise and the inoculum applied in the scoring, or even the cut ends may be inoculated. First stage mechanical pulp is a sterilized substrate and the invention may be applied generally to both sterilized and non-sterile substrates. However, particular and desired benefits are of course to be realized when the invention is used with non-sterile pulpwoods, including non-sterile refined pulpwoods. Dosage applied in practice of the present invention will not exceed $10^{10}$ CFU/Kg. of substrate with refined pulpwoods, and preferably are not in excess of $10^9$ CFU/Kg., and lower dosages may be used with more preferred embodiments.

The fungi of the present invention are of the species *Ophiostoma piliferum* and may be identified as such by established taxonomic procedures. As may be necessary or desired, the exact and total identity of particular strains, such as those deposited with NRRL in connection herewith, may be confirmed by known Restriction Fragment Length Polymorphism procedures (RFLP). The use of such procedures in fungus identification has been described in the literature, for example, by Raeder et al., Comparison of Lignin Degrading White Rot Fungi Phanerochaete Chrysosporium and *Sporotrichum pulverulentum* at the DNA Level, Curr: Genet. 8:499–506 (1984); by Wildeman et al., A CAT Family of Repetitive DNA Sequences in Saccharomyes Cerevisiae, J. Biol. Chem. 261, 13401–13403 (1986); and by All et al., DNA Fingering By Oligonucleotide Probes Specific For Simple Repeats, Human Genetics, 74, 239–243 (1986). Restriction enzymes we have found to be usually most suitable for *Ophiostoma piliferum* are PstI, Hind III and BamHI, with the repetitive sequence usually being $(CAT)_5$.

In-line sprayer

The in-line spray system for dispensing inoculum in large scale operations includes a 50 gallon tank, a motor driven propellor, and a pump. The 50 gallon tank acts as a reservoir of inoculum. A propellor inside the tank is used to provide the agitation required to keep the fungal cells in suspension. The pump withdraws the inoculum from the reservoir and dispenses the liquid at a rate of 25 gallons/minute to a series of 7 nozzles connected to best effect uniform discharge from each nozzle. The nozzles are attached 3 feet above a screw type conveyor having four one foot diameter screws in parallel across a bed which is five feet wide and four feet deep. The seven nozzles are organized in staggered fashion in two rows of four and three nozzles with 1.5 feet separating the two rows. The chips are advanced at about 60 feet/minute. The inoculated chips are discharged from the belt for evaluation storage at a point four feet past the last (3 nozzle) row.

What is claimed is:

1. A method of obtaining a fungus of the species *Ophiostoma piliferum* having the ability to grow white or colorless on a wood substrate comprising the steps of: a) mating fungi selected from each of the two *Ophiostoma piliferum* strains TAB 28 and TAB 51, b) selecting from said mating a non-white ascospore offspring which is of a mating type compatible with fungi of the *Ophiostoma piliferum* strain WZ58 and which has improved ability relative to both such parental strains to reduce the pitch content of sterilized Southern Yellow Pine wood chips in 14 days growth as determined by TAPPI Procedure T204 OS-76, c) mating the compatible non-white ascospore offspring selected in step b) with *Ophiostoma piliferum* strain WZ58; and d) selecting at least one ascospore offspring from the mating in step c) that grows white or colorless on sterilized Southern Yellow Pine wood chips, and has the ability to reduce pitch on Southern Yellow Pine wood chips at least as effectively as the non-white offspring selected under step b) when evaluated by TAPPI Procedure T204 OS-76 after 14 days growth.

2. The method of claim 1 in which the ascospore offspring selected in step d) degrades pitch on Southern Yellow Pine to a greater extent than the non-white ascospore offspring selected in step b) as determined by TAPPI Procedure T204 OS-76.

3. The method of claim 2 in which the ascospore offspring selected in step d) degrades pitch on sterilized aspen wood chips to a greater extent than WZ58.

4. A method of obtaining a fungus of the species *Ophiostoma piliferum* having the ability to grow white or colorless on a substrate of Southern Yellow Pine wood chips, said method comprising the steps of: a) mating fungi selected from each of the two *Ophiostoma piliferum* strains D3 and WZ58; and b) selecting from said mating at least one ascospore offspring which, when matured into a fungus, grows white or colorless on sterilized Southern Yellow Pine wood chips, and has the ability to reduce pitch on Southern Yellow Pine wood chips at least as effectively as the strain D3 when evaluated by TAPPI Procedure T204 OS-76 after 14 days growth.

5. The method of claim 4 in which the ascospore offspring selected in step b) degrades pitch on Southern Yellow Pine to a greater extent than WZ58.

6. The method of claim 5 in which the ascospore offspring selected in step b) degrades pitch on sterilized aspen wood chips to a greater extent than WZ58.

* * * * *